United States Patent
Giano et al.

(10) Patent No.: US 10,744,226 B2
(45) Date of Patent: Aug. 18, 2020

(54) HIGH-THROUGHPUT METHOD FOR DETECTING TOOTH STAIN PREVENTION AND REMOVAL

(71) Applicant: Johnson & Johnson Consumer Inc., Skillman, NJ (US)

(72) Inventors: Michael C. Giano, Southampton, NJ (US); Daniel Queiroz, Belle Mead, NJ (US); Susan Knox, Ewing, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/835,939

(22) Filed: Dec. 8, 2017

(65) Prior Publication Data

US 2019/0175783 A1  Jun. 13, 2019

(51) Int. Cl.
| | |
|---|---|
| *A61L 27/12* | (2006.01) |
| *A61K 6/00* | (2020.01) |
| *A61Q 11/00* | (2006.01) |
| *A61K 8/02* | (2006.01) |
| *G01N 21/17* | (2006.01) |
| *A61K 8/24* | (2006.01) |
| *G01N 1/30* | (2006.01) |
| *A61K 6/17* | (2020.01) |
| *A61K 6/52* | (2020.01) |

(52) U.S. Cl.
CPC ............... *A61L 27/12* (2013.01); *A61K 6/17* (2020.01); *A61K 6/52* (2020.01); *A61K 8/0241* (2013.01); *A61K 8/24* (2013.01); *A61Q 11/00* (2013.01); *G01N 1/30* (2013.01); *G01N 21/17* (2013.01); *A61K 2800/62* (2013.01)

(58) Field of Classification Search
CPC .......... A61K 6/52; A61K 8/24; A61K 8/0241; A61K 6/17; A61K 2800/62; G01N 21/17; G01N 1/30; A61L 27/12; A61Q 11/00
See application file for complete search history.

(56) References Cited

U.S. PATENT DOCUMENTS

| | | | |
|---|---|---|---|
| 6,682,722 B2 | 1/2004 | Majeti et al. | |
| 6,685,916 B1 | 2/2004 | Holme et al. | |
| 8,895,707 B2 * | 11/2014 | Cummings | .......... B01D 15/361 |
| | | | 530/412 |
| 9,562,254 B2 | 2/2017 | Potnis et al. | |
| 2006/0171907 A1 | 8/2006 | Scott et al. | |
| 2013/0344011 A1 | 12/2013 | Ramji et al. | |
| 2014/0113244 A1* | 4/2014 | Shiba | ..................... A61Q 11/00 |
| | | | 433/29 |
| 2014/0349253 A1 | 11/2014 | Shiba et al. | |
| 2017/0227512 A1 | 8/2017 | Utgikar et al. | |

FOREIGN PATENT DOCUMENTS

| | | |
|---|---|---|
| WO | WO 2015/134469 | 9/2015 |
| WO | WO 2016/074214 A1 | 5/2016 |

OTHER PUBLICATIONS

Langford et al. "Real-time monitoring of stain formation and removal on calcium hydroxyapatite surfaces using quartz crystal sensor technology", Analyst, 2002, 127, 360-367.*
International Search Report; PCT/US2018/063005; dated Feb. 14, 2019.

* cited by examiner

*Primary Examiner* — Lezah Roberts

(57) ABSTRACT

Provided are methods of detecting tooth stain prevention and/or removal comprising the steps of providing pellicle-coated hydroxyapatite particles, contacting the particles with a first solution and then a second solution, wherein the first solution is either a test solution or a stain solution and the second solution is the other of said test solution or stain solution, separating from the resulting particles a liquid comprising stain introduced in the contacting step b), and measuring the UV-Vis absorbance of the separated liquid to determine the amount of stain in the liquid.

9 Claims, 1 Drawing Sheet

HIGH-THROUGHPUT METHOD FOR DETECTING TOOTH STAIN PREVENTION AND REMOVAL

FIELD OF THE INVENTION

The present invention relates to a high-throughput assay for identifying molecules that prevent and/or remove tooth extrinsic stains.

BACKGROUND OF THE INVENTION

Tooth staining has many causes. These include the regular use of products that contain staining chemicals or color bodies such as foods, drinks (coffee, tea, cola, wine), or the use of tobacco. In other cases, medications, diseases, and poor dental hygiene may result in tooth staining. Staining affects the aesthetic appearance of teeth, and may also be a contributing factor to tooth decay and loss.

There have been many product formulations developed to prevent or remove stains from teeth. These include bleaches or oxidants, or oxidant free formulations. In the development of these formulations, significant testing is required to show formulation efficacy.

Some of the efficacy testing procedures developed use bovine or human teeth, or ceramic disks or powder specimens. In these procedures, a dental spectrophotometer is used to evaluate the color of the specimens both before and after immersion in the staining solutions (such as tea). Commission internationale de l'éclairage (CIE) L*a*b* color space values are recorded, and the change in color (ΔE*) is calculated. Staining is done either before or after the specimens are treated with the stain prevention or removal formulation. In the case of stain removal testing, the specimens are immersed in the staining solution before the specimens are treated with the stain removal formulation. In the case of stain prevention testing, the specimens are immersed in the staining solution after the specimens are treated with the stain prevention formulation.

In another test procedure, ceramic powder is placed in staining solution either before (removal testing) or after (prevention testing) exposure to the treatment solution. Then, the powder is dissolved away using acid, and the color change in the effluent is measured.

The above methods are labor intensive, and are therefore not high-throughput methods for screening the efficacy of formulations being tested for tooth stain prevention or removal.

What is needed is the development of high-throughput methods for detecting efficacy of tooth stain prevention or removal formulations.

SUMMARY OF THE INVENTION

According to one aspect the present invention provides methods of detecting tooth stain prevention and/or removal comprising the steps of providing pellicle-coated hydroxyapatite particles, contacting the particles with a first solution and then a second solution, wherein the first solution is either a test solution or a stain solution and the second solution is the other of said test solution or stain solution, separating from the resulting particles a liquid comprising stain introduced in the contacting step b), and measuring the UV-Vis absorbance of the separated liquid to determine the amount of stain in the liquid.

DETAILED DESCRIPTION OF THE INVENTION

Figure 1:
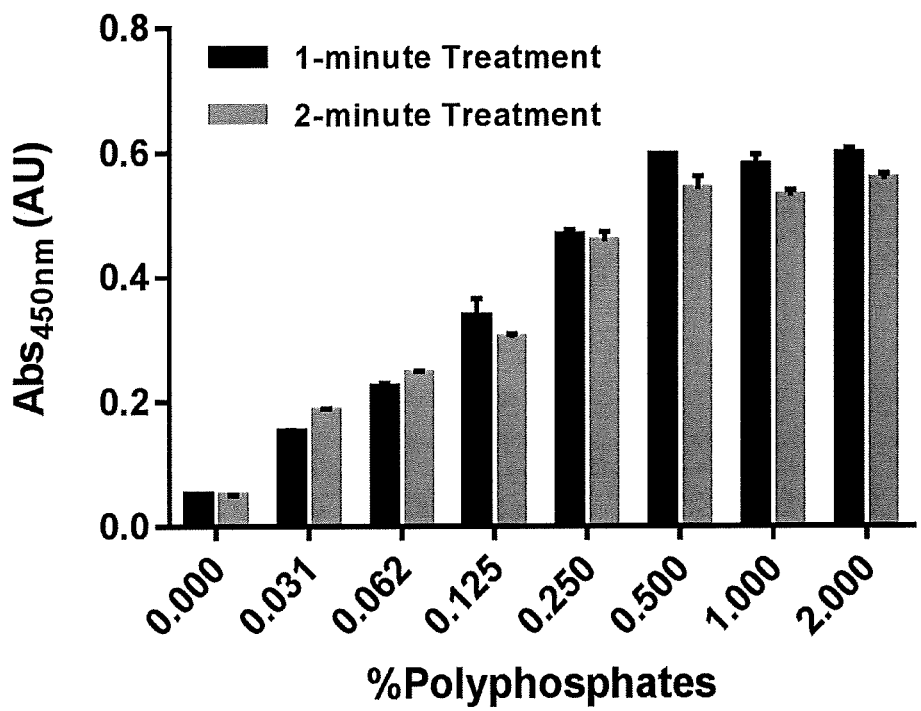
FIG. 1 shows absorbance values of stain removed from coffee stained, pellicle coated hydroxyapatite particles after exposed to a series polyphosphate solutions for 1- or 2-minute(s) of treatment.

Described herein, is a new high-throughput method for identifying molecules that prevent and/or remove tooth stain.

The methods of the present invention comprise the step of providing pellicle-coated hydroxyapatite particles for use in the method. Any suitable pellicle-coated hydroxyapatite particles, either sourced commercially or made as described herein, may be provided in accord with the present invention.

According to certain embodiments, the pellicle-coated hydroxyapatite particles are formed by coating hydroxyapatite particles ("HAp") with saliva to form the pellicle (protein coat). Preferably the process comprises mixing the hydroxyapatite particles with a saliva formulation and incubating the HAp/saliva suspension for a sufficient time to form a pellicle coat on hydroxyapatite particles.

Any suitable hydroxyapatite particles and saliva may be used. Suitable hydroxyapatite particles can range in size (diameter) from greater than about 3 micron to about 200 micron, or 10 micron to about 50 micron, or about 20 micron. A variety of hydroxyapatite particles are available commercially, for example, hydroxyapatite particles available from Bio-Rad. Saliva can be naturally derived or artificial. For example, suitable artificial saliva may be purchased from Northeast Laboratories (Berlin, Conn.) T0300).

The pellicle-coated HAp may be formed using any suitable amounts of HAp and saliva. In certain embodiments, the concentration range of HAp in saliva for formation is from about 0.1 to about 250 milligrams/milliliter, including from about 0.5 to about 200, from about 1 to about 150, from about 10 to about 150, from about 50 to about 150, and about 100 milligrams/milliliter of HAp in saliva. The HAp/saliva mixture may be incubated for any sufficient time, preferably at least 5 minutes, including at least 10 minutes or at least 15 minutes, and at any sufficient temperature, including from about 20 to about 60° C., including from about 30 to about 50, from about 30 to about 40, and about 37° C.

According to certain embodiments the pellicle coated HAp particle/saliva suspension resulting after incubation is filtered, with the saliva supernatant being sent to waste. The pellicle coated HAp particle/saliva suspension may then be transferred into a large batch filter container. The pore size of the filter container should be smaller than the size of the HAp particles. The filter container allows for easy separation of the solid HAp particles from supernatant, either by centrifugation or vacuum filtration. In one embodiment, the filter container can be a microfuge tube filter system that separates the supernatant from the particles by centrifugation with a relatively inert membrane and a pore size as low as 0.22 μm and as high as 5 μm. In another embodiment, the filter container can be a 96-well filter plate that separates supernatant from the particles by vacuum filtration with a relatively inert membrane and a pore size ranging from 0.22 μm to as high as 5 μm.

The provided pellicle-coated HAp particles are contacted in series with a first solution and a second solution, wherein the first solution is either a test solution or a stain solution and the second solution is the other of the test solution or stain solution. As will be readily apparent, in methods intended to measure the stain removal properties of a test solution, the pellicle-coated HAp are first contacted with a stain solution to stain the particles and then contacted with a test solution to determine its ability to remove such stain from the particles. Whereas, in a method to determine the ability of a test solution to prevent staining, the particles are first contacted with the test solution and subsequently contacted with the stain solution.

Stain Removal

According to certain preferred embodiments, the contacting step of the methods to determine stain removal may include the steps of contacting the pellicle-coated HAp with a first solution that is a stain solution. The result is a suspension of pellicle coated HAp particles and stain. Various stains can be either be store bought or prepared prior to the staining step, for example coffee, tea, wine, cola, polyphenols, iron, mixtures of two or more thereof, and the like. The concentration of stain in the stain solution can vary based on the type of stain. For example, for instant coffee the typical range is about 0.1 to about 20% w/v. For tea, the typical range is about 0.1 to about 10% w/v. Wine it can be used at 100%, or may be diluted with water. A concentration range of HAp particles in stain is between about 0.1 to about 10 milligrams/milliliter, or about 1 milligrams/milliliter. The particles/stain suspension is incubated to create stained particles. The mixture of HAp particles and stain solution should incubate at least 1 minute, or about 15 minutes, or about 30 minutes at a temperature between about 20° C. and about 60° C., or about 30° C. and about 50° C., or about 37° C.

The solution of stained HAp particles is filtered, with the stain supernatant preferably being sent to waste. In one embodiment, the stained HAp particles in stain solution are then transfer into a large batch filter container. As noted earlier, the pore size of the filter container should be smaller than the size of the HAp particles. Separation of the solid HAp particles from supernatant may be accomplished either by centrifugation or vacuum filtration. The stained particles may be rinsed with water, preferably until no more loosely bound stain is observed in the effluent. What remains in the filter container is preferably stained, pellicle coated HAp particles.

In certain embodiments, the stained, pellicle coated HAp particles are contacted with a test solution to determine the efficacy of the test solution for removing stain. In certain embodiments, the stained, pellicle coated HAp particles are re-suspended in deionized water to a concentration between about 0.1 to about 250 milligrams/milliliter, or about 10 to about 150 milligrams/milliliter, or about 100 milligrams/milliliter prior to contact with the test solution. In certain embodiments, the suspended HAp are contacted with a test solution within a short period of time, whereas in other embodiments, the suspension may be stored in a container, for example a 50-milliliter conical tube, until needed for stain removal testing.

The contacting step further comprising contacting the pellicle coated, stained HAp particles with a test solution comprising a stain removal formula or solution. The concentration of the stain removal solution is dependent on the stain removal formula and its removal ingredient(s). The treatment volume used per sample is between about 50 microliters and about 300 microliters, or between about 100 microliters and about 250 microliters, or about 200 microliters. The HAp particles are suspended in the stain removal solution, preferably with agitation during the treatment, to yield an HAp particle/stain removal suspension. The treatment time should be at least 10 seconds, or greater than about 30 seconds, or greater than about one minute, or greater than about 2 minutes. The incubation temperature is between about 20° C. and about 60° C., or about 25° C.

According to certain embodiments, the separating step comprises separating the used test fluid and any removed stain therein from the particles for measuring. In certain embodiments, the suspension of HAp particle and test solution/stain removal fluid resulting from the above step is filtered to separate such liquid from the particles and collected for further analysis. As will be recognized by one of skill in the art, the amount of stain in the separated fluid corresponds to stain removed from the stained particle by the test solution.

UV-Vis absorbance measurements in accord with the measuring step are performed on the fluid separated in the separating step. Any suitable UV-Vis apparatus and equipment may be used. For example, a multimode plate reader may be utilized to scan the absorbance between wavelengths 230 and 1000 nm. In the removal assay, a higher absorbance value at 450 nm is indicative of more stain removal, while a low absorbance value at 450 nm suggests minimal to no stain removal.

Stain Prevention

According to certain preferred embodiments, the contacting step of the methods to determine stain prevention may include the steps of contacting the pellicle-coated HAp with a first solution that is a test/stain prevention solution. The concentration of the stain prevention solution is dependent on the stain prevention formula and its prevention ingredient(s). The treatment volume used per sample, for example, may be between about 50 microliters and about 300 microliters, or between about 100 microliters and about 250 microliters, or about 200 microliters. The HAp particles are suspended in the stain prevention solution with agitation during the treatment to yield an HAp particle/stain prevention suspension. The treatment time should be at least 10 seconds, or greater than about 30 seconds, or greater than about two minutes, or greater than about 10 minutes. The incubation temperature is from about 20° C. to about 60° C., or about 20° C. to about 40° C., or about 25° C.

Next, the treated, pellicle coated HAp particle/saliva suspension is filtered to remove the treatment supernatant. As mentioned above, removal of the solid HAp particles from supernatant may be accomplished either by centrifugation or vacuum filtration. The treated particles may be rinsed with water until what remains in the filter container is pre-treated, pellicle coated HAp particles.

The pre-treated, pellicle coated HAp particles are next contacted with a second solution comprising stain. The result is a suspension of treated, pellicle coated HAp particles and stain. Any of the various stains and staining/incubating conditions as described above for stain removal can be used to stain the particles in the contacting step. The solution of stained HAp particles is preferably filtered to remove the supernatant stain fluid from the particles, and any loosely bound stain is washed off the pre-treated, pellicle coated HAp particles to provide stained, pre-treated pellicle coated HAp particles.

According to stain prevention embodiments, the step of separating fluid comprising stain for further analysis comprises eluting stain from the stained, pre-treated pellicle coated HAp particles and collecting the elute liquid comprising stain for analysis. The stain remaining on the particles, after the contacting step and filtration, is eluted with any suitable elute fluid, including, for example, high concentration polyphosphate solution. Examples of polyphosphates include pyrophosphate, tripolyphosphate, phytic acid, trimetaphosphate, hexametaphosphate. In some embodiments, pyrophosphates dissolved in water are used. Elute solution is mixed with the stained, pre-treated, pellicle coated HAp particles to create an HAp particle/polyphosphate suspension. The concentration range can be 1% to 10% w/v, or 5% w/v polyphosphate in water. The pH of the solution can be between pH 6 and 13, for example about 12. A volume range of 50 microliter to 300 microliter, or 200 microliter can be used to elute the stain. Incubation time of the eluent solution is at least about 30 seconds, or about one minute, or about five minutes, or about ten 10 minutes.

The pellicle coated, stained HAp particle/polyphosphate suspension is now filtered as described above, with one change being that the elution supernatant is collected for further analysis.

Finally, UV-Vis absorbance measurements are performed on the elution supernatant. A multimode plate reader may be utilized to scan the absorbance between wavelengths 230 and 1000 nm. In the prevention assay, a lower absorbance value at 450 nm is indicative of more stain prevention, while a high absorbance value at 450 nm suggests minimal to no stain prevention.

EXAMPLES

Example 1: Stain Removal Test

The following general procedure was used and described in more detail below:

Stain Removal Test Procedure:
1. Form a pellicle coat on hydroxyapatite (HAp) particles by mixing the particles with saliva and incubating the mixture.
2. Transfer HAp particle/saliva suspension into a large batch filter container.
3. Filter the saliva supernatant to waste.
4. Stain particles by adding a stain solution directly to the filter container and incubate.
5. Transfer stained, pellicle coated HAp particle suspension into filter container.
6. Filter the stained, pellicle coated HAp particles, sending the supernatant to waste.
7. Re-suspend stained, pellicle coated HAp particles in water, and optionally store for future testing.
8. Prepare stained, pellicle coated HAp particles for treatment.
9. Treat stained HAp particles.
10. Filter and collect the supernatant.
11. Make UV-Vis absorbance measurements on collected supernatant.

A mass of one gram of hydroxyapatite powder (Bio-Rad, Hercules, Calif., catalogue 1570020) was suspended in artificial saliva (Northeast Laboratories, Winslow, Me., catalogue no. T0300) at a concentration of 10 milligram/100 microliter and allowed to incubate for 15 minutes at 37° C. to form a pellicle coating. The supernatant was filtered out from the particles. The particles were re-suspended in 10% instant coffee stain solution at a concentration of 10 milligram/100 microliter and incubated at 37° C. for 30 minutes. The coffee solution was removed by filtration and the particles were washed of any loosely bound stain. The now coffee stained, pellicle coated hydroxyapatite particles were suspended in water at a concentration of 10 milligram/100 microliter. A volume of 100 microliter per sample was aliquoted into respective filter vesicle (96-well filter plate or filter tube) and the supernatant was filtered out from the particles (n=3 per sample). The treatment solutions were prepared within a range of 0% to 2% polyphosphate solution in water. The stock 2% w/v solution was serial diluted 1:1 in water to achieve treatment concentrations of polyphosphates of 1%, 0.5%, 0.25%, 0.125%, 0.0625%, and 0.03125% w/v. The 0% solution was a water control. After, the stained hydroxyapatite particles were exposed to 200 microliter of respective treatment for 1 or 2 minutes at room temperature with agitation (120 rpm). The polyphosphate treatment solutions ranged from 0.031% to 2% w/v. A negative control, using distilled water as the treatment solution, was tested as a comparison to the polyphosphate treatment solutions. Upon completion of the treatment, the stain removed into solution was separated from the particle and collected in a 96-well plate. Subsequently, absorbance measurements (Tecan, Infinite M200 Pro) were made between 230 and 1000 nm with a 10 nm step increase between measurements. The absorbance at 450 nm was used as a measure of stain removed, where higher absorbance values indicated more stain displaced from the hydroxyapatite particles.

FIG. 1 shows the 450 nm absorbance values of stain removed from coffee stained, pellicle coated hydroxyapatite particles as a function of the concentration of polyphosphate solutions for both 1- and 2-minute treatments. The figure shows a clear dose response for the polyphosphate solutions. As the concentration of polyphosphate solutions increased from 0.031% to 0.500%, stain removal increased. The level of stain removal remained constant from 0.500% to 2.00%. The figure also shows no significant difference between 1 or 2 minute treatments.

Example 2: Stain Prevention Test

The following general procedure is used and described in more detail below:

Stain Prevention Test Procedure:
1. Form a pellicle coat on hydroxyapatite (HAp) particles by mixing the particles with saliva and incubating the mixture.
2. Transfer HAp particle/saliva suspension into a large batch filter container.
3. Filter the saliva supernatant to waste.
4. Treat pellicle coated HAp particles, sending the supernatant to waste.
5. Filter the treated, pellicle coated HAp particles, sending the supernatant to waste.
6. Stain the pre-treated pellicle coated HAp particles by adding a stain solution directly to the filter container and incubate.
7. Wash any loosely bound stain off the pre-treated, pellicle coated HAp particles.
8. Elute the stain from the stained, pre-treated, pellicle coated HAp particles 5% PPi solution.
9. Filter and collect supernatant.
10. Make UV-Vis absorbance measurements on collected supernatant.

A mass of 1 gram of hydroxyapatite particles (Bio-Rad, Hercules, Calif., catalogue 1570020) was suspended in artificial saliva at a concentration of 10 milligram/100 microliter and allowed to incubate for 15 minutes at 37° C. to form a pellicle coating. A volume of 100 microliter per sample was aliquoted into respective filter vesicle (96-well filter plate or filter tube) and the supernatant was filtered out from the particles (n=3 per sample treatment). The treatment solutions were prepared within a range of 0% to 2% polyphosphate solution in water. The stock 2% w/v solution was serial diluted 1:1 in water to achieve treatment concentrations of polyphosphates of 1%, 0.5%, 0.25%, 0.125%, 0.0625%, and 0.03125% w/v. The 0% solution was a water control. The pellicle coated hydroxyapatite particles were exposed to 200 microliter of treatment solution of polyphosphate for at least 1 minute at room temperature with agitation (120 rpm). The treatment was removed by filtration and the particles were exposed to 100 microliter of a 10% instant coffee stain solution and incubated at 37° C. for 30 minutes. The coffee was removed by filtration and the particles were washed of any loosely bound stain. The residual stain on the particles was displaced with 200 microliter of an alkaline 5% pyrophosphate solution by incubating at room temperature for 10 minutes. The displaced stain was collected in a 96-well plate and absorbance measurements were made (Tecan, Infinite M200 Pro) between 230 and 1000 nm with a 10 nm step increase between measurements. The absorbance at 450 nm was used as a measure of stain prevention, with the lower absorbance values indicating more stain prevented from attaching to hydroxyapatite particle.

Figure 2:
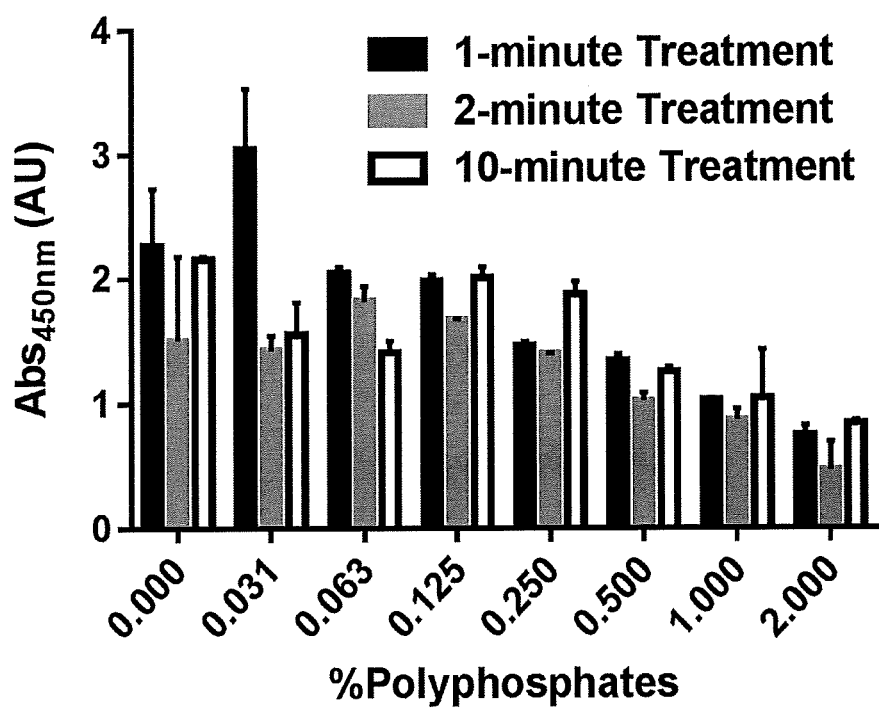
FIG. 2 shows absorbance values of stain displaced from hydroxyapatite particles after exposed to stain prevention pre-treatments.

FIG. 2 shows the 450 nm absorbance values of stain displaced from coffee stained, pellicle coated hydroxyapatite particles as a function of the concentration of polyphosphate solutions for 1-, 2-, and 10-minute stain prevention pre-treatments. The figure shows a clear dose response for the polyphosphate solutions. As the concentration of polyphosphate solutions increased from 0.031% to 0.500%, stain prevention increased. The level of stain removal remained constant from 0.500% to 2.00%. The figure also shows no significant difference for 1-, 2-, and 10-minute stain prevention pre-treatments.

What is claimed is:

1. A high-throughput method of detecting tooth stain prevention or removal comprising the steps of:
   a. providing pellicle-coated hydroxyapatite particles having a particle size of greater than about 3 micron to about 200 micron in a multi-well filter container,
   b. contacting said particles with a first solution and then a second solution in the multi-well filter container, wherein said first solution is either a test solution or a stain solution and the second solution is the other of said test solution or stain solution,
   c. separating from said particles from said solution comprising stain introduced in the contacting step b), and
   d. measuring the UV-Vis absorbance of the solution in a multimode plate reader separated in step c) to determine the amount of stain in such solution wherein the multi-well filter container and multimode plate reader are used to provide higher throughput.

2. The method of claim 1 wherein said providing step a comprises mixing said hydroxyapatite particles with saliva and incubating the mixture to form pellicle-coated hydroxyapatite particles.

3. The method of claim 1 wherein said method is to determine stain removal of a test solution and said contacting step b) comprises contacting said particles with a stain solution to form stained particles and then contacting said stained particles with said test solution.

4. The method of claim 3 wherein separating step comprises separating from said stained particles said test solution used to contact said particles in step b) and said measuring step comprises measuring the UV-Vis absorbance of the separated test fluid to determine the amount of stain in said test solution removed from the stained particles.

5. The method of claim 1 comprising the steps of:
   a. providing said pellicle-coated hydroxyapatite particles,
   b. contacting said particles with stain solution to form a suspension of stained, pellicle coated HAp particles and stain solution; filtering the stained, pellicle coated HAp particles from the stain solution; and contacting said stained, pellicle coated HAp particles with test solution to remove stain;
   c. separating said test solution comprising stain from said stained, pellicle coated HAp particles; and
   d. measuring the UV-Vis absorbance of the test solution separated in step c) to determine the amount of stain in such solution.

6. The method of claim 1 wherein said method is to determine stain prevention of a test solution and said contacting step b) comprises contacting said particles with a test solution to form pre-treated particles and then contacting said pre-treated particles with stain solution.

7. The method of claim 6 further comprising the step of removing stain solution from, and washing, the particles resulting from step b) to isolate stained, pre-treated particles.

8. The method of claim 7 wherein said separating step comprises eluting stain from said stained, pre-treated particles and collecting the eluent solution comprising stain for analysis.

9. The method of claim 1 comprising the steps of:
   a. providing said pellicle-coated hydroxyapatite particles,
   b. contacting said particles with a test solution to form pre-treated particles; filtering the pre-treated particles; and then contacting said filtered pre-treated particles with stain solution to stain the filtered pre-treated particles to form stained, pre-treated particles;
   c. elute the stain from the stained, pre-treated, particles;
   d. filter and collect eluent solution; and
   e. measure UV-Vis absorbance of collected eluent solution.

* * * * *